United States Patent
Sinnott (10) Patent No.: US 9,415,056 B2
(45) Date of Patent: Aug. 16, 2016

(54) PROCESSING OF NATURAL POLYSACCHARIDES BY SELECTED NON-PATHOGENIC MICROORGANISMS AND METHODS OF MAKING AND USING THE SAME

(75) Inventor: Robert A. Sinnott, Keller, TX (US)

(73) Assignee: MANNATECH, INC., Coppell, TX (US)

(*) Notice: Subject to any disclaimer, the term of this patent is extended or adjusted under 35 U.S.C. 154(b) by 617 days.

(21) Appl. No.: 12/118,604

(22) Filed: May 9, 2008

(65) Prior Publication Data

US 2008/0286252 A1 Nov. 20, 2008

Related U.S. Application Data

(60) Provisional application No. 60/917,339, filed on May 11, 2007.

(51) Int. Cl.

| A61K 31/7016 | (2006.01) |
|---|---|
| A61K 31/702 | (2006.01) |
| A61K 31/736 | (2006.01) |
| C12P 19/00 | (2006.01) |
| A61K 35/741 | (2015.01) |
| A61K 36/886 | (2006.01) |
| A23L 1/052 | (2006.01) |
| A23L 1/30 | (2006.01) |
| A61K 31/7004 | (2006.01) |
| A61K 31/715 | (2006.01) |
| A61K 35/745 | (2015.01) |
| A61K 35/747 | (2015.01) |
| C12P 19/02 | (2006.01) |
| C12P 19/04 | (2006.01) |
| C12P 19/12 | (2006.01) |

(52) U.S. Cl.
CPC ............ *A61K 31/7016* (2013.01); *A23L 1/052* (2013.01); *A23L 1/3002* (2013.01); *A23L 1/3014* (2013.01); *A61K 31/7004* (2013.01); *A61K 31/715* (2013.01); *A61K 31/736* (2013.01); *A61K 35/741* (2013.01); *A61K 35/745* (2013.01); *A61K 35/747* (2013.01); *A61K 36/886* (2013.01); *C12P 19/02* (2013.01); *C12P 19/04* (2013.01); *C12P 19/12* (2013.01); *A23V 2002/00* (2013.01)

(58) Field of Classification Search
CPC ............ A61K 31/7016; A61K 31/736; A61K 31/7004; A61K 31/715; A61K 35/745; A61K 35/741; A61K 35/747; A61K 36/886; C12P 19/02; C12P 19/12; C12P 19/04; A23L 1/052; A23L 1/3002; A23L 1/3014
See application file for complete search history.

(56) References Cited

U.S. PATENT DOCUMENTS

| 5,292,511 | A | * | 3/1994 | Kim et al. ................. 424/744 |
|---|---|---|---|---|
| 5,902,796 | A | * | 5/1999 | Shand et al. ................ 514/54 |
| 5,928,664 | A | | 7/1999 | Yang et al. |
| 6,060,050 | A | | 5/2000 | Brown et al. |
| 6,203,797 | B1 | * | 3/2001 | Perry .................... 424/93.45 |
| 6,241,983 | B1 | | 6/2001 | Paul et al. |
| 6,383,482 | B1 | * | 5/2002 | Gorsek .................. 424/93.45 |
| 6,468,525 | B1 | | 10/2002 | Watson et al. |
| 6,586,032 | B2 | | 7/2003 | Grazela et al. |
| 6,783,780 | B1 | | 8/2004 | De Jong et al. |
| 6,797,266 | B2 | | 9/2004 | Naidu |
| 6,864,231 | B2 | | 3/2005 | Chokshi |
| 6,942,856 | B2 | | 9/2005 | Chokshi |
| 7,138,113 | B2 | | 11/2006 | Chokshi |
| 7,172,777 | B2 | | 2/2007 | Schmitt et al. |
| 2003/0072770 | A1 | * | 4/2003 | McAnalley et al. ..... 424/195.18 |
| 2003/0137067 | A1 | * | 7/2003 | Cooper et al. ................ 264/5 |
| 2003/0185811 | A1 | | 10/2003 | Teasdale et al. |
| 2004/0005304 | A1 | | 1/2004 | Brudnak |
| 2004/0023360 | A1 | | 2/2004 | Lacroix et al. |
| 2004/0071824 | A1 | | 4/2004 | Van Laere et al. |
| 2004/0115308 | A1 | * | 6/2004 | Bengtsson-Riveros et al. ........................ 426/61 |
| 2005/0070500 | A1 | | 3/2005 | Boucher l et al. |
| 2005/0074442 | A1 | | 4/2005 | Ranganathan |
| 2005/0079244 | A1 | | 4/2005 | Giffard et al. |
| 2005/0271758 | A1 | | 12/2005 | Farmer |
| 2005/0288250 | A1 | | 12/2005 | Rautonen et al. |
| 2006/0057131 | A1 | | 3/2006 | Simard et al. |
| 2006/0093592 | A1 | | 5/2006 | Cheruvanky et al. |
| 2006/0105063 | A1 | | 5/2006 | Hann et al. |
| 2006/0228448 | A1 | | 10/2006 | Boileau et al. |
| 2007/0059296 | A1 | | 3/2007 | Chen |

(Continued)

FOREIGN PATENT DOCUMENTS

| CN | 1596124 A | 3/2005 | | |
|---|---|---|---|---|
| DE | 19730538 A1 | * | 1/1999 | ................ A23L 2/52 |
| KR | 0128714 B1 | | 4/1998 | |
| WO | 89/01970 A2 | | 3/1989 | |
| WO | 9502689 A1 | | 1/1995 | |
| WO | 9847374 A1 | | 10/1998 | |
| WO | 03026687 A1 | | 4/2003 | |
| WO | 03075891 A1 | | 9/2003 | |
| WO | 03095659 A1 | | 11/2003 | |
| WO | WO 2005111195 A2 | * | 11/2005 | ............. A61K 35/74 |
| WO | 2006/012586 A2 | | 2/2006 | |

OTHER PUBLICATIONS

Ni et al. Aloe polysaccharides. Aloes:the genus *Aloe*. edited by Tom Reynolds. CRC press 2004, p. 1-13.*

(Continued)

*Primary Examiner* — Taeyoon Kim
(74) *Attorney, Agent, or Firm* — Edwin S. Flores; Chalker Flores, LLP (57) ABSTRACT

The present invention includes compositions and methods of making and using a dietary supplement manufactured from one or more natural polysaccharides previously incubated with a probiotic bacteria in a bioreactor system, wherein the bacteria process the polysaccharides and the resulting processed polysaccharide are provided in the nutritional supplement.

10 Claims, 4 Drawing Sheets

(56) References Cited

U.S. PATENT DOCUMENTS

2007/0071817 A1    3/2007    Rau
2007/0071871 A1    3/2007    Shrikhande et al.
2007/0098784 A1    5/2007    Moger

OTHER PUBLICATIONS

Gibson et al. Dietary Modulation of the Human Colonie Microbiota: Introducing the Concept of Prebiotics. J. Nutr. 125: 1401-1412, 1995.*

Comstock, L.E., et al., Bacterioides thetaiotaomicron: a dynamic, niche-adapted human symbiont. BioEssays (2003), 25:926-929.

Drisko, et. al. "Probiotics in Health Maintenance and Disease Prevention." Alternative Medicine Review (2003), 8 (2):143-155.

Ferencik M, et al. "Successful modification of human intestinal microflora with oral administration of lactic acid bacteria." Bratisl. Lek.Listy. (1999), 100 (5):238-245.

Habermann W, et al. "Reduction of acute recurrence in patients with chronic recurrent hypertrophic sinusitis by treatment with a bacterial immunostimulant (Enterococcus faecalis Bacteriae of human origin)," Arzneimittelforschung. (2002), 52 (8):622-627. (Abstract only).

Hlivak, P., et al. "Long-term (56-week) oral administration of probiotic Enterococcus faecium M-74 decreases the expression of sICAM-1 and monocyte CD54, and increases that of lymphocyte CD49d in humans." Bratisl.Lek.Listy. (2005), 106 (4-5):175-181.

Hlivak, P., et al. "One-year application of probiotic strain Enterococcus faecium M-74 decreases serum cholesterol levels." Bratisl.Lek. Listy. (2005), 106 (2):67-72.

Hooper, et. al. "A molecular sensor that allows a gut commensal to control its nutrient foundation in a competitive ecosystem." Proceedings of the National Academy of Sciences (USA) (1999), 96:9833-9838.

Hooper, et. al. "Angiogenins: a new class of microbicidal proteins involved in innate immunity." Nat Immunol (2003), 4:269-273.

Mazmanian, et. al. "An Immunomodulatory Molecule of Symbiotic Bacteria Directs Maturation of the Host Immune System." Cell (2005), 122:107-118.

Moreno, M.R., et al. "The role and application of enterococci in food and health," Int J Food Microbiol. (2006), 106 (1):1-24.

Salyers, et. al. "Fermentation of Mucins and Plant Polysaccharides by Anaerobic Bacteria from the Human Colon." Applied and Environmental Microbiology (1977), 34:529-533.

Salyers, et. al. "Digestion of Larch Arabinogalactan by a strain of Human Colonic Bacterioides Growing in Continuous Culture." J. Agric. Food Chem. (1981), 29:475-480.

Stappenbeck, et. al. "Developmental regulation of intestinal angiogenesis by indigenous microbes via Paneth cells." Proceedings of the National Academy of Sciences (USA) (2002), 99:15451-15455.

Xu J, et al., "Honor thy symbionts." Proc Nat Acad Sci USA. (2003), 100 (18):10452-10459.

Zhou, L., et al., "Study on the processing technology of aloe gelyogurt," (2005) Food Science and Technology.

Ebringer, et al., "Beneficial Modification of the Human Intestinal Microflora Using Orally Administered Lactic Acid Bacteria", Bratisl Lek Listy, 1999; 100 (5) 238-245.

IRS PCT/US2008/063329 (ISA/US) Dated Aug. 5, 2008.

\* cited by examiner

PROCESSING OF NATURAL POLYSACCHARIDES BY SELECTED NON-PATHOGENIC MICROORGANISMS AND METHODS OF MAKING AND USING THE SAME

CROSS-REFERENCE TO RELATED APPLICATIONS

This application claims priority to U.S. provisional application Ser. No. 60/917,339 filed on May 11, 2007, the entire contents of which are incorporated herein by reference.

TECHNICAL FIELD OF THE INVENTION

The present invention relates in general to the field of probiotic organisms, and more particularly, to compositions and methods for the delivery of dietary supplements that have been treated and processed by pro-biotic organisms.

BACKGROUND OF THE INVENTION

Without limiting the scope of the invention, its background is described in connection with probiotic organisms.

Probiotic organisms can have a number of positive effects on health. Often, the probiotic organisms are provided such that they enter and colonize portions of the digestive tract. Probiotics compete against local organisms that have previously colonized the digestive tract. These local organisms inhibit colonization by other microorganisms and in some cases can be deleterious to the development of a healthy digestive flora. Many probiotic organisms are presently available that are ingested to attempt to establish a desirable, positive intestinal flora. However, the effectiveness of the probiotic cultures that are ingested to attempt to compete against the local organisms is often limited by the ability of the organisms to reach the target site, outcompete the local organisms, establish stable colonization and compete for nutrients against pre-existing organisms. The problem with undesirable digestive organisms is that they often become increasingly resistant to antibiotics, become well established in the intestinal mucosa, have had an opportunity to adapt to the local environment, effectively compete for nutrients and are not transported out of the digestive tract.

One such invention that attempts to address the problem of probiotic colonization is taught in U.S. Pat. No. 7,172,777, issued to Schmitt, et al. for a powder for preparation of a probiotic yogurt food. Briefly, Schnitt teaches a powder for preparation of a probiotic yogurt food that contains probiotic cultures with a prespecified proportion of living probiotic lactic-acid bacteria and a thermogenetic-lipolytic resorption-enhancing agent, in particular pepper extract, to intensify the resorptive processes in the intestine, as well as a capillary-dilating agent, in particular nicotinic acid, to achieve dilation of the capillaries in the intestinal tract.

Yet another invention is taught in U.S. Pat. No. 6,468,525, issued to Watson, et al., for a probiotic formulation useful as a food supplement and a material for reestablishing beneficial bacteria to the body's intestinal tract that includes a mixture of beneficial probiotic microflora comprising *lactobacillus acidophilus, bifidobacterium bifidum, lactobacillus salivarius, bifidobacterium infantis*, and *bifidobacterium longum*, fructooligosaccharides, L-glutamine, and N-acetyl glucosamine.

Yet another invention is taught in U.S. Pat. No. 6,203,797, issued to Perry for a dietary supplement and method for use as a probiotic, for alleviating the symptoms associated with irritable bowel syndrome. The dietary supplement taught is a probiotic and for alleviating symptoms of irritable bowel syndrome, that includes freeze-dried aloe, fructo-oligosaccharides, and dahlia inulin juice mixture and optionally vitamin B6 (pyridoxine) manganese and L-glutamine. An additional alternate embodiments specifically for alleviation of symptoms of irritable bowel syndrome, including in the base formula bromelain and papain. Also for specific probiotic functions the following friendly bacteria: *Lactobacillus bulgaricus, lactobacillus acidophilus, lactobacillus plantarum*, and *Bifidobacterium bifidum* could be added to the base formula.

U.S. Pat. No. 6,060,050 issued to Brown, et al., teaches probiotic composition for inclusion in food products to enhance their nutritional value. The composition includes one or more probiotic microorganisms such as *Bifidobacterium* and a carrier to transport the microorganisms to the large bowel or other regions of the gastrointestinal tract. The carrier is a modified or unmodified resistant starch, particularly a high amylose starch, which acts as a growth or maintenance medium for microorganisms in the large bowel or other regions of the gastrointestinal tact.

United States Patent Application No. 20070059296, teaches a probiotic composition having acid-resistant enteric coating that includes 15 to 20 wt % of milk powder, 25 to 30 wt % of corn starch, 8 to 15 wt % of modified starch (capsule), 10 to 15 wt % of ethylcellulose, 5 to 15 wt % of bacterial broth, and 10 to 15 wt % of talc. The probiotic composition is microencapsulated to form a plurality of microencapsule coated with an acid-resistant enteric coating for improving the enteric acid-resistance, the probiotic survival rate, the antimicrobial property, the stability, the moisture-proof property, and the mobility of the probiotic composition preventing from coagulation in a moist environment and for being used as an additive applied to livestock feed.

SUMMARY OF THE INVENTION

Despite many attempts of re-creating the digestive flora by delivery of various forms pro-biotic organisms, through various delivery methods and in various amounts, the need remains for dietary supplementation of organisms with bio-available nutrients. The present inventor recognized that absent changes in digestive flora and/or during the rebuilding of favorable digestive flora, a need remains for the nutrients that these symbiotic microorganisms produce from the food consumed by the host. Symbiotic digestive tract microorganisms provide the host with a number of advantageous functions, including: fermenting unused energy substrates; activating the immune system; preventing the growth of non-symbiotic or harmful species; producing vitamins and nutrient precursors for the host (including biotin and vitamin K), and producing certain hormones or hormone-precursors.

The present invention relates generally to novel methods and compositions for utilizing microbial species to biologically process natural polysaccharides into useful products that have utility as dietary supplements or foods. The present invention includes combining natural polysaccharides with selected probiotic bacteria in a bioreactor system and having the bacteria process the polysaccharides outside the body. The products of the bioreactor are then used to prepare a food or dietary supplement. In another embodiment of the present invention a dosage form of selected natural polysaccharides and selected, non-pathogenic (probiotic) microbial species are combined to provide nutritional supplementation while at the same time delivering the necessary pro-probiotic nutrients and symbiotic organisms. By dosing these substances simultaneously into the human GI tract, the processing of the polysaccharide by the non-pathogenic microbial species into other beneficial products may be accomplished within the confines of the human gastrointestinal tract.

The novel products produced from this microbial processing of selected polysaccharide components are expected to have useful effects on human health including: (1) improving GI tract and systematic immune functioning by interaction with the mucosal-associated lymphoreticular tissues (MALT); (2) weight management and reduction of obesity by: (a) improving GI tract digestion and nutrient absorbtion efficiency; (b) reduction of undesirable microbial species within the human GI tract; and (c) interaction of introduced probiotic microorganisms and polysaccharide products with various control factors (i.e. hormone receptors) within the human GI tract; and/or (3) improving blood lipid parameters such as cholesterol reduction and reducing triglyceride levels.

In one aspect the present invention is a dietary supplement that includes a supplement manufactured from one or more natural polysaccharides previously incubated with a probiotic bacteria in a bioreactor system, wherein the bacteria process the polysaccharides and the resulting processed polysaccharide are provided in the nutritional supplement. In one embodiment the processed polysaccharide obtained from the bioreactor are adapted into a food or dietary supplement, e.g., are adapted into a single dosage form. The polysaccharides for use with the invention may include at least one of glucomannans, aloe glucomannan, konjac glucomannan, galactomannans, arabinogalactans, larch arabinogalactans, algal polysaccharides, fucoidans, fungal polysaccharides, fungal glucomannans, gum tragacanth, gum ghatti, xanthan gum, guar gum, and gum acacia. In one embodiment, the polysaccharides and viable microbial cells are provided separately in a single dosage form. In another embodiment, polysaccharides and viable microbial cells are incubated in a bioreactor. The polysaccharides and viable microbial cells may also be provided in a sustained release form. Examples of polysaccharides include heteropolysaccharides, homopolysaccharides or both. In one example of the dietary supplement, the polysaccharides are isolated away from the microbial cells, and the isolated polysaccharides are loaded into a dosage form selected from powder, capsule, gelcap, tablet, effervescent tablet, liquid or gummy.

In another aspect, the present invention is a probiotic food or dietary supplement formulation comprising one or more natural polysaccharides and viable microbial cells of at least one of *Lactobacillus, Lactococcus, Streptococcus, Enterococcus, Leuconostoc, Acetobacter, Candida, Kluveromyces, Saccharomyces, Torula, Torulaspora, Debaryomyces, Zygosaccharomyces, Bacterioides, Bacillus, Bifidobacterium, Eubacterium, Peptostreptococcus, Ruminococcus* and *Pediococcus*. The polysaccharides may be at least one of glucomannans, aloe glucomannan, konjac glucomannan, galactomannans, arabinogalactans, larch arabinogalactans, algal polysaccharides, fucoidans, fungal polysaccharides, fungal glucomannans, gum tragacanth, gum ghatti, xanthan gum, guar gum, and gum acacia. In one embodiment, the polysaccharides and viable microbial cells are provided separately in a single dosage form. In another embodiment the polysaccharides and viable microbial cells are incubated in a bioreactor. In yet another embodiment, the polysaccharides and viable microbial cells are provided in a sustained release form.

In another aspect, the present invention is a dietary supplement comprising the extract from the processing of selected natural polysaccharides by non-pathogenic, probiotic microbial species in a bioreactor. In yet another aspect, the present invention includes a method of making a dietary supplement by mixing one or more natural polysaccharides with a probiotic bacteria in a bioreactor system under conditions that stimulate the processing by the bacteria of the natural polysaccharides to make processed polysaccharides; and preparing the dietary supplement after at least a portion of the natural polysaccharides have been processed by the bacteria. In one embodiment, the bacteria process the polysaccharides and the resulting processed polysaccharides are manufactured into a single dosage nutritional supplement. In one embodiment, the method further includes the steps of isolating the processed polysaccharides from the natural polysaccharides and the bacteria; and preparing a dosage form comprising the processed polysaccharides. In another embodiment, the method further includes the step of preparing a dosage form comprising the processed polysaccharides, the natural polysaccharides and the bacteria. In another embodiment, the method further includes the processed polysaccharides are loaded into a dosage form selected from powder, capsule, gelcap, tablet, effervescent tablet, liquid or gummy. In another embodiment, the processed polysaccharides are isolated away from the bacteria, and the processed polysaccharides are loaded into a dosage form selected from powder, capsule, gelcap, tablet, effervescent tablet, liquid or gummy.

In another aspect the present invention is a dietary supplement or food product that includes a processed Aloe vera inner leaf gel incubated with a probiotic bacteria in a bioreactor or fermentor system, wherein the bacteria process the Aloe vera inner leaf gel into a bioavailable product. In one embodiment, the probiotic bacteria include at least one bacteria selected from *Lactobacillus, Lactococcus, Streptococcus, Enterococcus, Leuconostoc, Acetobacter, Candida, Kluveromyces, Saccharomyces, Torula, Torulaspora, Debaryomyces, Zygosaccharomyces, Bacterioides, Bacillus, Bifidobacterium, Eubacterium, Peptostreptococcus, Ruminococcus* and *Pediococcus* or combinations thereof.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "nutritionally effective amount" is used to define the amount that will provide a beneficial nutritional effect or response in a mammal. For example, as nutritional response to dietary supplements varies from mammal to mammal, it should be understood that nutritionally effective amounts of the natural polysaccharides with selected probiotic bacteria will vary, respectively. The present invention includes both the natural polysaccharides that have been processed by the probiotic bacteria separate from the probiotic bacteria (at least partially isolated away from the probiotic bacteria), combined with inactivated probiotic bacteria and the natural polysaccharides and the probiotic bacteria.

The skilled artisan will recognize that certain individuals will benefit from one or more of the combined formulations that are natural polysaccharides that have been pre-processed by the pro-biotic bacteria (e.g., those that have normal digestive flora, those that are not in need of additional pro-biotic supplementation and even those that are avoiding the probiotic bacteria). Likewise, the lack of natural polysaccharides with selected probiotic bacteria are known to affect physiological and cellular functions.

The nutritionally effective amount of the natural polysaccharides with selected probiotic bacteria disclosed herein serve to preserve and/or elevate the levels of these critical nutrients in the diet of, e.g., a human that seeks to maintain or augment their diet for these nutritional supplements. Thus, while one mammal may require a particular profile of natural polysaccharides with selected probiotic bacteria present in defined amounts, another mammal may require the same particular profile of vitamins and minerals present in different defined amounts.

As used herein, the terms "saccharides," "polysaccharides," "natural polysaccharides", "glyconutritional" or "glyconutrient" refer to carbohydrates, polysaccharides, oligosaccharides, disaccharides or monosaccharides, whether branched or linear, derivatized or underivatized, whether complex or simple that may be obtained from natural sources and are necessary for the biochemical synthesis of various classes of communication and signal molecules that may be free in interstitial cellular fluids, active in cell to cell communication (i.e., cytokines, growth factors, etc.), or constitute the molecular configuration comprising loci of highly specific molecular activity of cell membranes (i.e., receptor sites, ion-transport channels, antigenic identification, and the like).

The natural saccharides of the invention can be found in nature as mono-, oligo- and/or polysaccharides. Thus, the compositions of the invention can contain the saccharides in their monomeric, oligomeric and/or polymeric forms. For a list of known natural sources for the natural polysaccharides and their uses, please refer to U.S. Patent Application No. US2003072770, relevant saccharides and sources of saccharides incorporated herein by reference.

In some embodiments, the active agents of the present invention may be prepared for delivery in a modified or delayed release form. For example, when the agent is acid sensitive, the agent may be delivered with an enteric coating to reach the intestinal tract before release. As used herein, the terms "modified release," "extended release" and "controlled release" describe one or more release profiles to effect delivery of a nutritionally effective amount of a nutrient over an extended period of time, defined herein as being between about 60 minutes and about 2, 4, 6, 8 or more hours using the formulation of the present invention. Modified release may also be defined functionally as the release of over 80 to 90 percent (%) of the nutrient after about 60 minutes and about 2, 4, 6, or even 8 hours. The release may also be evaluated by making the natural vitamins or natural minerals available to the user regardless of uptake, as some actives may never be absorbed by the animal. Various modified release dosage forms may be designed readily by one of skill in art as disclosed herein to achieve delivery to both the small and large intestines, to only the small intestine, or to only the large intestine, depending upon the choice of coating materials and/or coating thickness.

Examples of modifications that can be made to the long-chain polysaccharides include, e.g., changing the types or composition of saccharides in the long-chain polysaccharides, chemically modifying (organically or chemically) the side chains of the saccharides (e.g., acetylation), hydrolyzing the long-chain polysaccharides, sizing the long-chain polysaccharides, polymerizing longer long-chain polysaccharides, selecting combinations of shorter and longer long-chain polysaccharides, separating the long-chain polysaccharides by, e.g., electroporation, FPLC, HPLC, size-exclusion, size-exclusion chromatography, precipitation and the like. Extended release formulations may be prepared and delivered so that release is accomplished at some generally predictable location in the lower intestinal tract more distal to that which would have been accomplished if there had been no modified release alterations.

As used herein, the term "carbohydrate" is used interchangeably with the terms "saccharide," "polysaccharide," "oligosaccharide" and "sugar" the definitions of which are well known to those skilled in the art of carbohydrate chemistry. Although the compositions of the invention are intended to include at least two or more essential saccharides, it should be noted that the saccharides can be in the form of mono-, oligo- and/or polysaccharides, e.g., a composition containing gum tragacanth and guar gum will be considered as containing galacturonic acid, sialic acid, mannose and galactose. Therefore, by controlling the amount of particular gums in a given dietary supplement, one can control the amount of the respective saccharides in the dietary supplement.

As used herein the term "isolated" refers to an organic molecule or group of similar molecules that have been subjected to fractionation to remove various other components and that retain substantially its expressed biological activity. Where the term "substantially purified" is used, this designation will refer to a composition in which the active form of the nutrients of the composition constitute about 10%, 20%, 30%, 40%, 50%, 60%, 70%, 80%, 90%, 95% or more of the total molecules in the composition. In some cases the active form of the nutrient can not be successfully removed from its normal cellular milieu without affecting its activity. In fact, the present invention takes advantage of the natural processing of polysaccharides by probiotic microbes in a bioreactor to deliver the highest quality and quantity of active, nutritional compounds. However, in some cases a balance is achieved between the level of processing or "isolation", the effectiveness of the compound and the overall cost and impact on the environment. The skilled artisan will recognize that it is possible to maximize the effectiveness of the compound while at the same time being responsible stewards of the environment. In the case of plants, e.g., native plants, a balance must also be maintained with the local culture and community to minimize the impact of the production of plants that include the nutritional compounds isolated for use with the present invention.

Techniques and compositions for making useful dosage forms of the natural polysaccharides and probiotic bacteria using the present invention are described in one or more of the following references: Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.), and the like, relevant portions incorporated herein by reference.

For example, the compositions of the present invention may be included in a tablet. Tablets may contain, e.g., suitable binders, lubricants, disintegrating agents, coloring agents, flavoring agents, flow-inducing agents, gummy agents, chewing agents and/or melting agents. For example, oral administration may be in a dosage unit form of a tablet, gelcap, caplet or capsule, the active drug component being combined with a non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, dicalcium phosphate, and mixtures thereof, and the like. Disintegrators may include: starch, methyl cellulose, agar, bentonite, xanthan gum, mixtures thereof, and the like.

The poly-, oligo-, di- or mono-saccharides included in the dietary supplement of the present invention are available from a wide variety of natural and synthetic sources such as shrubs, trees, plants, yeasts, fungi, molds, gums, resins, starch and cellulose derivatives and natural mucin sources. Non-limiting examples of some of the natural sources of polysaccharides for use with the present invention include: (a) shrub or tree exudates which contain acacia, karaya, tragacanth, or ghatti; (b) marine gums which include agar, algin, or carrageenan; (c) seed gums which include guar, locust bean, or psyllium; (d) plant extracts which contain pectins or acetylated polymannose; (e) starch and cellulose derivatives such as carboxymethylcellulose, ethylcellulose, hydroxypropyl methylcellulose, methylcellulose, oxidized cellulose; and microbial gums which contain dextrans, and xanthan. However, it should be recognized that the composition of the invention is not intended to be limited by the source from which the respective saccharides are obtained.

As used herein, the terms "plant-derived", "plant powders", "plant extract" and "herbal extract" are used interchangeably to refer to natural sources of poly-, oligo-, di- or mono-saccharides that are produced in plant tissues and that can be processed by the pro-biotic microorganisms of the present invention. The natural sources for the natural sources of poly-, oligo-, di- or mono-saccharides that form part of the present invention are typically isolating at least a part of the plant away from its natural state, e.g., by removing water (e.g., extracting the juice and/or pulp), extracting one or more components chemically, mechanically, thermally, by size or otherwise separating the components using polar, non-polar, mineral, petroleum or other solvents, and that have some degree of beneficial health or therapeutic activity. The isolation of the active agent from the plant will depend on the nature of the active agent, e.g., water soluble, insoluble, miscible and the like, sensitivity to decomposition (e.g., denaturation by heat, pH, oxygen, light, etc.). Plant extracts also include dehydrated plant materials in which the bulk liquid is removed to concentrate the bioavailable solids in the plant or herb. Most herbal agents can be toxic, especially when concentrated, but are generally safe when utilized in their more traditional manner in teas and poultices as a "folk medicinal for the treatment of disease and promotion of good health."

Probiotics are live non-pathogenic and non-toxigenic microbial species, including *Lactobacillus* species, *Bifidobacteria* species and yeasts, which can be either natural constituents of the gastrointestinal (GI) tract microflora or can be introduced into the population of the GI tract microflora via supplementation with certain foods or dietary supplements. Probiotics may beneficially affect the host organism upon ingestion by improving the balance of intestinal microflora. Some recent research suggests that certain live microorganisms may have immunomodulatory and anticarcinogenic effects as well as other health benefits. Some microflora of the GI tract also complete the digestion of certain food substances by processes such as fermentation. Intestinal microflora are important for maturation of the immune system, the development of normal intestinal morphology, and in order to maintain a chronic and immunologically balanced inflammatory response. The microflora reinforce the barrier function of the intestinal mucosa, preventing the attachment of pathogens and the entry of allergenic substances. There is currently much active scientific research into targeted probiotics, which use well-characterized bacteria that are selected for specific health-enhancing effects. Currently, various species of *Bifidobacterium* and *Lactobacillus*, as well as *Lactococcus lactis, Streptococcus thermophilus, Enterococcus faecium* and *Saccharomyces boulardii* are recognized in the Physician's Desk Reference (PDR) as probiotics.

Powders. The probiotic-processed polysaccharides may be provided in powder form. The powder form may also include the pro-biotic bacteria or portions thereof as disclosed herein. Often, the powder form may also include one or more carriers, excipients, wettability agents, flowability agents, flavors, colorants and the like that increase the look, feel and even help preserve the powder.

Capsules. Capsules may be prepared by filling standard two-piece hard gelatin capsules each with 1 to 1000 milligrams of probiotic-processed polysaccharides. The capsules may be filled with excipients, carriers and the like, e.g., 0.5 to 150 milligrams of lactose, 0.1 to 500 milligrams of cellulose and 0.1 to 60 milligrams magnesium stearate. The capsule may also include pro-biotic bacteria as disclosed herein.

Soft Gelatin Capsules. A mixture of probiotic-processed polysaccharides is dissolved in a digestible oil such as soybean oil, cottonseed oil, or olive oil, and the like. The probiotic-processed polysaccharides and injected by using a positive displacement pump into gelatin to form soft gelatin capsules containing, e.g., 100-500 milligrams of the probiotic-processed polysaccharides. The softgel capsules are washed and dried. The softgel capsule may also include pro-biotic bacteria as disclosed herein.

Tablets. Tablets are prepared by conventional procedures so that the dosage unit has 100-500 milligrams of probiotic-processed polysaccharides, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption. The tablets may also include pro-biotic bacteria as disclosed herein.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the probiotic-processed polysaccharides, drug and/or salt thereof, conventional beading or filling agents and, optionally, sweeteners, flavors and lubricants. The effervescent tablets may also include pro-biotic bacteria as disclosed herein.

Suspension. An aqueous suspension is prepared for oral administration so that each 5 ml contain 100 mg of finely divided probiotic-processed polysaccharides, 200 mg of sodium carboxymethyl cellulose, 5 mg of sodium benzoate, 1.0 g of sorbitol solution, U.S.P., and 0.025 ml of vanillin. The suspension may also include pro-biotic bacteria as disclosed herein.

For mini-tablets, the probiotic-processed polysaccharides are compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

For a gummy consumable, the present invention may be combined with the teachings of, e.g., U.S. Pat. No. 5,928,664, issued to Yang, et al., relevant portions incorporated herein by reference. Briefly, a consumable gummy delivery system is taught in which the present invention is combined into a gummy delivery systems that includes an probiotic-processed polysaccharides admixed with a glycerylated gelatin matrix prepared by heating an aqueous solution of gelatin and glycerin to a temperature and for a time sufficient to remove some of the moisture content of the initial aqueous solution. The probiotic-processed polysaccharides taught herein can be delivered from a shearform matrix carrier. For a plant-based formulation to provide a "gummy consistency", the present invention may use the compositions and methods taught in, e.g., U.S. Pat. No. 6,586,032 issued to Grazela, et al., relevant portions incorporated herein by reference. Briefly, a gelatin-free gummy confection using gellan gum and carrageenan, which provides a firm, resilient, gelatin-like texture in a gelatin-free gummy confection. The gummy consumable may also include probiotic bacteria as disclosed herein.

It is also known that certain species of the GI tract microflora, such as *Bacterioides thetaiotaomicron*, produce enzymes that may aid in the digestion of substances, such as beta-bonded plant fibers, which can not be broken down by the normal digestive enzymes produced by humans. *Bacterioides thetaiotaomicron* apparently accomplishes this by producing beta-glucosylhydrolase enzymes. The production of these enzymes and other substances appears to be induced by exposure to specific polysaccharide substrates. It is notable that some of these enzymes are reported to be secreted extracellularly. Some recent studies have also revealed a role for *Bacterioides thetaiotaomicron* for inducing host molecule fucosylation, stimulating angiogenesis and inducing an innate immune response in the gut. Another species of *Bacteroides*, *Bacteroides fragilis*, has recently been shown to produce a bacterial polysaccharide (PSA), which directs the cellular and physical maturation of the developing immune system of mice. This is significant since *Bacterioides* species are among the earliest-colonizing and most numerically prominent of the gut microflora. Specifically, *Bacteroides fragilis* is an ubiquitous and important Gram-negative anaerobe that colonizes the mammalian lower gastrointestinal tract.

The release of extracellular beta-glucosylhydrolase enzymes by bacterial species such as *Bacterioides thetaiotaomicron* may result in degradation of beta-bonded polysaccharides into smaller polysaccharides, oligosaccharides, and simple monosaccharide and disaccharide sugars. In fact, the ability of *Bacterioides thetaiotaomicron* to grow in continuous culture using Larch arabinogalactans, which contains small, medium and long-chain polysaccharides, has been demonstrated. These enzymatic digestion products might then be available for absorbtion and utilization by other microbes or be absorbed by the human body via the intestines. While intracellular fermentation of polysaccharides by certain microbial species, such as *Enterobacteria* and lactic acid-producing bacteria, has been extensively studied, the actual biological significance of extracellular enzymatic digestion by bacteria such as *Bacterioides thetaiotaomicron* within the human GI tract has apparently not been extensively explored.

A lactic acid bacterium, *Enteroccus* is ecologically versatile and able to tolerate a wide range of temperatures and pH conditions. It colonizes the human small and large intestines. The two bacterial species best able to compete for all three IPs in this study, *E. faecalis* and *E. faecium*, are popular probiotics. Human probiotic supplementation studies have documented that both species can stimulate the immune system. *E. faecium* has also been shown to decrease serum cholesterol and reduce the expression of cell receptors involved in the inflammatory response.

Prebiotics are food ingredients that stimulate the growth or activity of certain GI tract microorganisms. Commercially available prebiotics are generally indigestible polysaccharides of plant origin that are selectively utilized, via anaerobic fermentation metabolizm, by certain beneficial lactic acid bacteria such as *Bifidobacteria* and *Lactobacillus* species. Some commonly employed probiotics include inulin, fructooligosaccharides (FOS), and Jerusalem artichoke.

Example 1

Selection of Probiotic Cultures for Enhanced Growth on Selected Polysaccharide Substrates Different species and strains of bacteria, that are present within the human GI tract, have the ability to utilize different polysaccharide substrates. For example, in a study of 154 strains from 22 different species of *Bifidobacterium*, *Peptostreptococcus*, *Lactobacillus*, *Ruminococcus*, *Coprococcus*, *Eubacterium*, and *Fusobacterium* were surveyed for their ability to ferment 21 different complex carbohydrates. The common food polysaccharides starch (amylose) and amylopectin were fermented by the most bacterial strains in the survey. At least some strains in 7 of the 22 species surveyed were able to utilize amylose and/or amylopectin. Other polysaccharides such as D-galactosamine, dextran, gum karaya, fucoidan, alginate, carrageenan, chondroitin sulfate, hyaluronate, heparin, ovomucoid, and beef submaxillary mucin were not fermented by any of the strains tested. The other polysaccharides included in the survey, glucosamine, fucose, xylan, larch arabinogalactan, gum guar, gum locust bean, gum arabic, gum ghatti, gum tragacanth, pectin, polygalacturonate, and laminarin were fermented selectively by certain bacterial strains but not by others. This study shows that it is possible to select bacterial strains from the human GI tract for the selective processing, via fermentation, of selected polysaccharides.

Cultured foods such as, fermented vegetables, yogurt, kefir, ymer, buttermilk and laban use various microorganisms to create food for human consumption.

A wide variety of bacterial and yeast species are safely used in the production of these food products. These microbes, with long histories of safe use in human foods are excellent candidates to screen for their ability to process purified long-chain polysaccharide compounds into smaller biologically active compounds such as shorter polysaccharides, oligosaccharides, disaccharides and monosaccharides. Such processing could be engineered to occur either in vivo by combining one or more of these microorganisms with natural polysaccharides in a form whereby both components are simultaneously administered orally to humans or other animals. In this first example, the processing of the polysaccharide by the microorganism would occur during transit through GI tract. Alternately, the microorganism and the polysaccharide could be combined in a mechanical fermentation apparatus under controlled physical conditions (i.e. nutrients, temperature, hydrogen ion concentration, oxidation/reduction potential, oxygen availability, water activity, salt concentration, etc.) and incubated until the desired final end products (i.e. acceptable ratios of shorter polysaccharides, oligosaccharides, disaccharides, and monosaccharides) are produced.

Typical microorganisms found in kefir grains, which are stable mixed cultures of various bacteria and yeasts, include:
*Lactobacillus acidophillus*
*Lb. brevis*
*Lb. casei*
*Lb. lactis*
*Lb. plantarum*
*Lb. paracasei*
*Lb. cellobiosus*
*Lb. delbrueckii*
*Lb. fructivorans*
*Lb. helveticus*
*Lb. hilgardii*
*Lb. kefiri*
*Lb. kefiranofaciens*
*Lb. kefirgranum*
*Lb. parakefir*
*Lactococcus lactis*
*Streptococcus salivarius*
*S. thermophilis*
*S. lactis*
*Enterococcus durans*
*Leuconostoc cremoris*
*Leuc. mesenteroides*
*Acetobacter aceti*
*A. rasens*
*Candida kefir*
*C. pseudotropicalis*
*C. rancens*
*C. tenuis*
*Kluveromyces lactis*
*K. marxianus*
*K. bulgaricus*
*K. fragilis*
*Saccharomyces kefir*
*S. cervisiae*
*S. lactis*
*S. carlsbergensis*
*S. unisporus*
*S. rouxii*
*Torula kefir*
*Torulaspora delbrueckii*
*Debaryomyces hansenii*
*Zygosaccharomyces rouxii*

Some typical bacteria used in the fermentation of vegetables and dairy products include:
*Lactobacillus acidophilus*
*L. bulgaricus*
*L. plantarum*
*L. lactis*
*L. delbrueckii*
*L. leichmannii*
*L. salivarius*
*L. caret*
*L. pentoaceticus*
*L. brevis*
*L. buchneri*
*L. cellobiosus*
*L. confusus*
*L. coprophilus*
*L. fermentatum*
*L. sanfrancisco*
*L. thermophilus*
*L. bavaricus*
*L. casei*
*L. coryniformis*
*L. curvatus*
*L. plantarum*
*L. sake*
*Leuconostoc dextranicum*
*Leu. mesenteroides*
*Leu. paramesenteroides*
*Enterococcus faecium*
*Enterococcus faecalis*
*Pediococcus acidilactici*
*Pediococcus damnosus*
*Pediococcus pentocacus*

Example 2

Additional Agents for the Enhancement of Probiotic Organism Growth and Polysaccharide Utilization Inclusion of additional agents, other than polysaccharides, which foster the growth of beneficial bacteria or inhibit the growth of competing bacteria, either in vivo or in vitro may be beneficial. Examples of these additional substances could include:

(1) selective antibiotic substances, which inhibit the growth of gram-negative bacteria while having a lesser effect on gram-positive bacteria, such as *Lactobacillus* and *Bifidobacteria*

(2) selective antibiotic substances, which inhibit the growth of gram-positive bacteria while having a lesser effect on gram-negative bacteria, such as *Bacterioides* species (3) substances which stimulate the growth of probiotic bacteria such as sub-bituminous humic substances, which have been used in animal feeds to stimulate the growth of beneficial bacteria (4) substances, such as inorganic or organic acids and bases, which change alter the pH conditions of the growth system to favor the growth of beneficial, probiotic microorganisms (5) substances, such as hydride ion and/or other chemicals with chemical reduction potential, which alter the oxidation-reduction conditions of the growth system to favor the growth of beneficial anaerobic microorganisms such as *Bacterioides, Lactobacilli* and *Bifidobacteria*

Example 3

Compositions and Methods for Selecting and Making Probiotic-Processed Polysaccharides with or without Probiotics

*Bacterioides thetaiotaomicron*

A probiotic food or dietary supplement formulation comprising a natural polysaccharide(s) and viable cells of *Bacterioides thetaiotaomicron*

A probiotic food or dietary supplement formulation comprising a natural polysaccharide(s) and viable cells of *Bacterioides thetaiotaomicron* and selected growth-promoting agents, which stimulate the growth of gram-negative anaerobes A method for producing bacterially-modified polysaccharides, oligosaccharides, disaccharides, and monosaccharides using *Bacterioides thetaiotaomicron* to effect enzymatic degradation of naturally occurring polysaccharides in a closed bioreactor system A method for producing bacterially-modified polysaccharides and oligosaccharides with immunological activity using *Bacterioides thetaiotaomicron* to effect enzymatic degradation of naturally occurring polysaccharides in a closed bioreactor system

*Bacterioides fragilis*

A probiotic food or dietary supplement formulation comprising a natural polysaccharide(s) and viable cells of *Bacterioides fragilis*

A probiotic food or dietary supplement formulation comprising a natural polysaccharide(s) and viable cells of *Bacterioides fragilis* and selected growth-promoting agents, which stimulate the growth of gram-negative anaerobes A method for producing bacterially-modified polysaccharides, oligosaccharides, disaccharides, and monosaccharides using *Bacterioides fragilis* to effect enzymatic degradation of naturally occurring polysaccharides in a closed bioreactor system A method for producing bacterially-modified polysaccharides and oligosaccharides with immunological activity using *Bacterioides fragilis* to effect enzymatic degradation of naturally occurring polysaccharides in a closed bioreactor system

*Bifidobacterium longum*

A probiotic food or dietary supplement formulation comprising a natural polysaccharide(s) and viable cells of *Bifidobacterium longum*

A probiotic food or dietary supplement formulation comprising a natural polysaccharide(s) and viable cells of *Bifidobacterium longum* and selected growth-promoting agents, which stimulate the growth of anaerobes A method for producing bacterially-modified polysaccharides, oligosaccharides, disaccharides, and monosaccharides using *Bifidobacterium longum* to effect enzymatic degradation of naturally occurring polysaccharides in a closed bioreactor system A method for producing bacterially-modified polysaccharides and oligosaccharides with immunological activity using *Bifidobacterium longum* to effect enzymatic degradation of naturally occurring polysaccharides in a closed bioreactor system

*Enterococcus faecium*

A probiotic food or dietary supplement formulation including a natural polysaccharide(s) and viable cells of *Enterococcus faecium*

A probiotic food or dietary supplement formulation including a natural polysaccharide(s) and viable cells of *Enterococcus faecium* and selected growth-promoting agents, which stimulate the growth of gram-negative anaerobes A method for producing bacterially-modified polysaccharides, oligosaccharides, disaccharides, and monosaccharides using *Enterococcus faecium* to effect enzymatic degradation of naturally occurring polysaccharides in a closed bioreactor system A method for producing bacterially-modified polysaccharides and oligosaccharides with immunological activity using *Enterococcus faecium* to effect enzymatic degradation of naturally occurring polysaccharides in a closed bioreactor system Various probiotic bacteria.

Selection of specific, non-pathogenic food processing microorganisms from the group: *Lactobacillus, Lactococcus, Streptococcus, Enterococcus, Leuconostoc, Acetobacter, Candida, Kluveromyces, Saccharomyces, Torula, Torulaspora, Debaryomyces, Zygosaccharomyces, Bacterioides, Bacillus, Bifidobacterium, Eubacterium, Peptostreptococcus, Ruminococcus* and *Pediococcus* with the ability to utilize polysaccharides selected from the group: glucomannans, aloe glucomannan, konjac glucomannan, galactomannans, arabinogalactans, larch arabinogalactans, algal polysaccharides, fucoidans, fungal polysaccharides, fungal glucomannans, gum tragacanth, gum ghatti, xanthan gum, guar gum, and gum acacia and combinations thereof for the production of polysaccharides, oligosaccharides, disaccharides and monosaccharides Combination of one or more polysaccharides chosen from the group of: glucomannans, aloe glucomannan, konjac glucomannan, galactomannans, arabinogalactans, larch arabinogalactans, algal polysaccharides, fucoidans, fungal polysaccharides, fungal glucomannans, gum tragacanth, gum ghatti, xanthan gum, guar gum, and gum acacia with viable cells of non-pathogenic microbial species selected from the group: *Lactobacillus, Lactococcus, Streptococcus, Enterococcus, Leuconostoc, Acetobacter, Candida, Kluveromyces, Saccharomyces, Torula, Torulaspora, Debaryomyces, Zygosaccharomyces, Bacterioides, Bacillus, Bifidobacterium, Eubacterium, Peptostreptococcus, Ruminococcus* and *Pediococcus* to produce a probiotic dietary supplement or food A method for producing partially-degraded polysaccharides, oligosaccharides, disaccharides, and monosaccharides using non-pathogenic microbial species selected from the group: *Lactobacillus, Lactococcus, Streptococcus, Enterococcus, Leuconostoc, Acetobacter, Candida, Kluveromyces,*

Saccharomyces, Torula, Torulaspora, Debaryomyces, Zygosaccharomyces, Bacterioides, Bacillus, Bifidobacterium, Eubacterium, Peptostreptococcus, Ruminococcus and Pediococcus to effect enzymatic degradation of naturally occurring polysaccharides chosen from the group of: glucomannans, aloe glucomannan, konjac glucomannan, galactomannans, arabinogalactans, larch arabinogalactans, algal polysaccharides, fucoidans, fungal polysaccharides, fungal glucomannans, gum tragacanth, gum ghatti, xanthan gum, guar gum, and gum acacia in a closed bioreactor system A method for producing partially-degraded polysaccharides and oligosaccharides with immunological activity using non-pathogenic microbial species selected from the group: Lactobacillus, Lactococcus, Streptococcus, Enterococcus, Leuconostoc, Acetobacter, Candida, Kluveromyces, Saccharomyces, Torula, Torulaspora, Debaryomyces, Zygosaccharomyces, Bacterioides, Bacillus, Bifidobacterium, Eubacterium, Peptostreptococcus, Ruminococcus and Pediococcus to effect enzymatic degradation of naturally occurring polysaccharides chosen from the group of: glucomannans, aloe glucomannan, konjac glucomannan, galactomannans, arabinogalactans, larch arabinogalactans, algal polysaccharides, fucoidans, fungal polysaccharides, fungal glucomannans, gum tragacanth, gum ghatti, xanthan gum, guar gum, and gum acacia in a closed bioreactor system.

The benefits of some medicinal plants that have been popular for much of human history may in part be attributed to their immunomodulatory polysaccharide (IP) content. For example, the immunomodulatory activities of Echinacea purpurea, Panax ginseng, and Curcma longa can be partially attributed to their arabinogalactan content. Polysaccharides in aloe vera gel, particularly the acetylated mannans, are also potent immunomodulatory substances. The following is an example of one embodiment of the present invention.

In vitro, immunomodulatory polysaccharides (IPs) can activate macrophages, stimulate the proliferation of T-cell and B-cells, suppress complement activity, modulate cytokine release and stimulate the intestinal immune system. Polysaccharides of higher molecular weight (MW) have more potent immunomodulatory effects. Following oral ingestion IPs can be used as adjuvant therapies for cancer patients-prolonging survival and improving quality of life. When ingested, complex plant polysaccharides (CPPs) typically enter the intestines largely intact, where they may then be degraded to varying degrees by the complex microflora in the gut. These substances can thereby impact the composition and density of the bacterial flora and generate monosaccharides, short-chain fatty acids, CPP fragments and metabolites, and gases. These CPP degradation products can then impact the GI immune system and be absorbed or excreted. The in vitro demonstration described below illustrates the human colonic bacterial utilization of a mixed-saccharide dietary supplement (MSS) formulated for immune system support and two of its CPP constituents: arabinogalactan (LAG) and high molecular weight aloe vera gel polysaccharides (AVP). The demonstration selected for colonic bacteria best able to compete for CPPs as energy sources and as material for the manufacture of more bacteria.

The following preparations are typical polysaccharide for use with the present invention.

Weighed samples of CPPs (Larch arabinogalactan); high molecular weight aloe vera gel polysaccharides; a mixed saccharide dietary supplement (AdvancedAmbrotose™ which includes: LAG, AVP, Anogeissus latifolia stem gum, Astragalus gummifer stem gum, glucosamine HCl and Undaris pinnatifida extract) were thoroughly mixed in deionized water on an orbital shaker for four hours at 200 rpm. Suspensions were 7.63-7.9 g/L. 100 ml of each suspension was then dialyzed in 6,000-8,000 MWCO tubing for 20 h at 4° C. against a volume of approximately 10 L of $diH_2O$. $diH_2O$ was changed twice during the 20 h period. Dialyzed samples were first frozen for one hour at 0° C. before being freeze dried.

Fecal samples were provided by 4 healthy human. Subjects were chosen with ages younger than 45, with total diet including <25% of fast food, did not take antibiotics within the last 12 month, had no GI problems in the last 5 years, do not have irregular bowel movements, did not use OTC medicines for constipation, stomach or bowel cramps, or diarrhea, did not have food poisoning in the last 6 months and do not worry about getting sick. Fecal samples were confirmed negative for the following pathogens: Clostridium difficile, Salmonella, Shigella, Campylobacter, Vibrio, Yersinia, and E. coli O157. Ten grams of fecal samples were mixed with 750 ml Brain Heart Infusion and mixed in a blender for four 30 second pulses before 6 hour incubation at 37° C. One ml aliquots were stored in 20% glycerol at 80 degrees C. prior to use. On the day of demonstration, an aliquot was thawed rapidly in warm water and then added to 2 ml of anaerobic E media (0.2%) w/v citric acid, 1% wlv $K_2HPO_4$, 0.35% w/v $NaNH_4HPO_4.4\ H_2O$ and 0.002% w/v $MgSO_4.7H_2O$) and incubated for 48 hours before addition to E media containing CPPs. CPPs were suspended by agitation for 2 h in $diH_2O$ and then added to anaerobic E media to achieve a final composition of 1% w/v. Under anaerobic conditions, 20 µl of fecal suspension was added to 2 ml of the CPP in E media suspension and left to incubate for 3 days under anaerobic conditions ($CO_2$ gas pack) at 37° C. One control example set consisted of fecal suspension added to E media without CPP was included to evaluate the effects of CPPs in E media, another control example set with the CPPs in E media for 9 days under culture conditions. After three days of incubation (i.e., day 3), 20 µl of the culture was added to 2 ml of fresh CPP in E media. This was repeated again on day 6. At the end of 9 days, bacteria were collected by centrifugation and snap-frozen in a dry ice-ethanol slurry. Supernatants were saved and evaluated for chemical composition by HPLC refraction detection. Control example sets were processed in an identical manner except that they were not inoculated with feces. Day nine bacteria were harvested and processed for 16s rDNA identification.

Bacteria identification by 165 rDNA sequencing. On the ninth day, samples were streaked onto bacterial growth media plates for isolation. Medias used were: 1) Difco™ Lactobacillus MRS agar, 2) Bifidobaeceria MRS with NNLP (naladixic acid, neomycin, lithium chloride and paramomycin sulphate), 3) MRS with 4% NaCl, 4) MRS with 2% bile salts, and 5) MRS at pH 5.2. A total of 57 isolates were selected from the passages of the four fecal cultures. DNA was extracted from isolates using the BactReady Kit (GenScript; Piscataway, N.J.) according to manufacturer's instructions. The PCR amplification of the purified DNA was performed using TaKaRa SpeedSTAR HS DNA polymerase reagents and universal primers for 16S rDNA amplification, forward F8-5'-AGAGTTTGATCCTGGCTCAG-3' (SEQ ID NO:1) and reverse R1492-5' GGTTACCTTGTTACGACTT-3' (SEQ ID NO:2). The conditions for the PCR amplification were 94° C. for 15 minutes; 35 cycles of 94° C. for 40 seconds and 60° C. for 30 seconds; and 72° C. for 2 minutes, followed by a 4° C. hold. Purity of products was confirmed by running 2 μl on a 2% agarose E-gel. Amplicons were sequenced by Alpha Biolabs. The resulting sequences were subjected to BLAST searches and the best match reported. Biochemical testing Gram stains were performed on each isolate using a kit according to the manufacturer's instructions. Hemolysis was determined by isolated colony growth on Difco™, tryptic-soy agar plates containing 5% sheep's blood agar. Oxidase production was determined by using the oxidase reagent according to manufacturer's instructions. Catalase production was determined by the ability of isolates to produce bubbles in hydrogen peroxide. The identifications were confirmed using API Strep or API20 E strips according to manufacturer's instructions.

Figure 1:
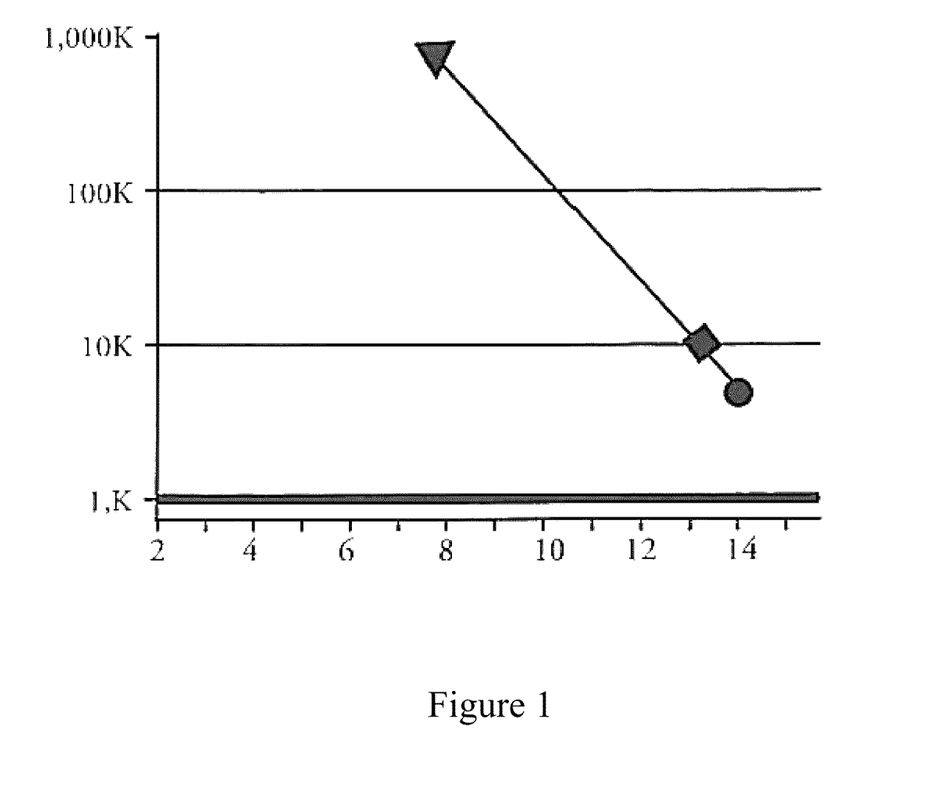
FIG. 1 is diagram of HPLC retention time of 5,000, 10,000 and 800,000 polymaltotriose MW standards with y-axis being MW and x-axis being retention time in minutes.

Chemical analysis of bacterial supernatants. Supernatants were thawed at room temperature, added to deionized water and filtered with 0.2 μm polypropylene Mini UniPrep™ filters before HPLC analysis. Separation on the basis of molecular size was evaluated using BioSep-SEC-S-4000 column tion of the MW of CPPs and supernatants (FIG. 1). FIG. 1 is diagram of HPLC retention time of 5,000, 10,000 and 800,000 polymaltotriose MW standards with y-axis being MW and x-axis being retention time in minutes.

RESULTS. Bacteria. The sequencing analysis yielded 52 isolates of the *Enterococci* genus, 4 isolates of *Escherichia coli* and one isolate of *Klebsiella pneumoniae*. The sequence analysis had confidence (>93%) to the genus level of all isolates and to the species level of 40 isolates. Further identification and confirmation of bacterial species and phenotypic characteristic were obtained by biochemical profiling using commercially available API testing strips and conventional microbiological testing methods. The sequence identification, gram stain, oxidase and catalase results were used to determine the appropriate API testing strip, API 20 Strep for the Entercocci and API 20 E for the enteric isolates. The resulting strip information was evaluated using the API database and the resulting identification was determined (Table I).

TABLE 1 below shows the biochemical characteristics of *Enterococci* species isolates cultured from fecal samples grown in specific CPP media. The values are represented as percent positive for each demonstration.

TABLE 1

Biochemical characteristics of Enterococci species isolates

|  | Enterococcus faccalis | Enterococcus faecium | Enterococcus durans | Enterococcus avium |
|---|---|---|---|---|
| Number of isolates | 2 | 46 | 1 | 3 |
| CPP | LAG | LAG, AVP, MSS | LAG | AVP |
| Gram Stain | +cocci | +cocci | +cocci | +cocci |
| Beta Hemolysis | 50% | 0% | 0% | 0% |
| Catalase | 0% | 0% | 0% | 0% |
| Oxidase | 0% | 0% | 0% | 0% |
| API 20 Strep Strip nTests | | | | |
| Voges Proskauer | 100% | 97.8% | 100% | 100% |
| Hippuric acid hydrolysis | 100% | 86.9% | 0% | 33.3% |
| Esculin Hydrolysis | 100% | 100% | 100% | 100% |
| Pyrrolidonyl Arylamidase | 100% | 97.8% | 100% | 33.3% |
| Alpha-Galaccosidase | 0% | 67.4% | 100% | 33.3% |
| Beta-Glucuronidase | 0% | 0% | 0% | 0% |
| Beta-Galactosidase | 50% | 100% | 100% | 0% |
| Alkaline Phosphatase | 100% | 43.5% | 100% | 66.6% |
| Leucine Aminopeptidase | 100% | 95.6% | 100% | 100% |
| Arginine Dehydrolase | 100% | 100% | 100% | 0% |
| Ribose | 100% | 100% | 100% | 100% |
| Arabinose | 50% | 97.8% | 0% | 100% |
| Mannitol | 100% | 100% | 0% | 100% |
| Sorbitol | 100% | 36.9% | 0% | 100% |
| Lactose | 100% | 100% | 100% | 100% |
| Trehelose | 100% | 100% | 100% | 100% |
| Insulin | 0% | 4.3% | 100% | 100% |
| Raffinose | 0% | 82.6% | 0% | 33.3% |
| Amidon | 100% | 80.4% | 100% | 66.6% |
| Glycogen | 0% | 0% | 0% | 0% |

HPLC. 5,000; 10,000; and 800,000 polymaltotriose MW Standards were added to deionized water (about 1 mg/ml) and analyzed by HPLC to confirm that CPP dialysis had eliminated smaller saccharides (<6,000 MW) and to allow estima- The *Enterococci* were *Enterococcus faecium* (46), *Enterococcus faecalis* (2), *Enterococcus durans* (1), and *Enterococcus avium* (2). In accordance with previously published information, all isolated *Enterococcus* species were gram positive, catalase negative, oxidase negative and positive for the hydrolysis of esculin. Only 5 of the 52 isolates were beta hemolytic on blood agar. 100% of *E. faecium* and *E. durans*, and 50% of *E. faecium* were positive for beta-galactosidase, the enzyme necessary for arabinogalactan hydrolysis. 100% of *E. faecium* and 50% of *E. faecalis* were able to ferment arabinose, a major monosaccharide in arabinogalactan. *E. durans* could not ferment arabinose.

*E. coli* isolates (4) were found only in the cultures using LAG. A single *Klebsiella pneumoniae* isolate was recovered from the AVP culture. Table 2 below shows the metabolic profiling results from *E. coli* and *Klebsiella pneumoniae* isolates. These enteric bacteria are gram negative bacilli that are catalase positive and oxidase negative. Only one isolate of *E. Coli* was identified as beta hemolytic.

TABLE 2 below lists the biochemical characteristics of the enteric bacteria isolated from fecal samples grown on CPP media. The values are represented as percent positive for each.

TABLE 2

Biochemical characteristics of the enteric bacteria.

|  | *Escherichia coli* | *Klebsiella pneumoniae* |
|---|---|---|
| Number of isolates | 4 | 1 |
| IP | LAG | AVP |
| Gram Stain | −bacilli | −bacilli |
| Beta Hemolysis | 25% | 0% |
| Catalase | 100% | 100% |
| Oxidase | 0% | 0% |
| API 20 E Test Strip Tests | | |
| Beta-galactosidase | 0% | 0% |
| Arginine Dihydrolase | 25% | 100% |
| Lysine Decarboxylase | 75% | 0% |
| Ornithine Decarboxylase | 25% | 0% |
| Gitrate Utilization | 0% | 0% |
| Hydrogen Sulfide Production | 0% | 0% |
| Urease | 0% | 0% |
| Tryptophane Deaminase | 0% | 0% |
| Indole Production | 75% | 0% |
| Voges Proskauer | 25% | 0% |
| Gelatinase | 0% | 0% |
| Glucose | 100% | 0% |
| Mannitol | 75% | 0% |
| Inositol | 0% | 0% |
| Sorbitol | 75% | 0% |
| Raffinose | 75% | 0% |
| Saccharose | 75% | 0% |
| Melibiose | 75% | 0% |
| Amygdalin | 25% | 0% |
| Arabinose | 75% | 0% |

Figure 2:
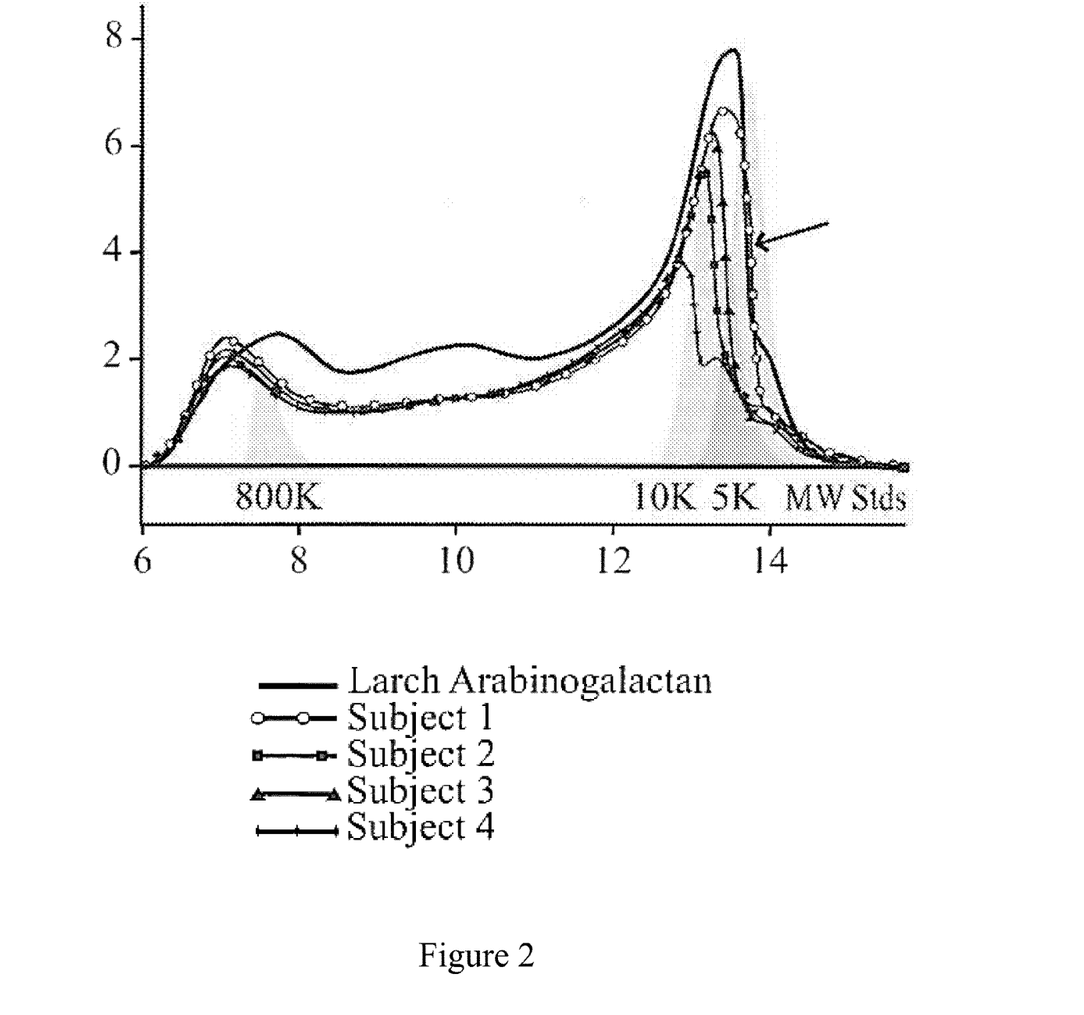
FIG. 2 is a diagram showing Larch arabinogalactan (LAC) end products following 72 hours incubation with 4 subjects' human colonic bacteria.

Supernatants. There were notable losses of CPPs in all molecular weight ranges relative to a control that was incubated for 9 days under conditions identical to those used for bacterial culture. However, losses were variable and were dependent on the CPP and fecal sample. All four subjects' fecal cultures consumed LAG polymers equally well between the ranges of 800,000 to approximately 12,000 MW. Polymers less than 12,000 MW, however, were consumed in differing amounts (FIG. 2). FIG. 2 is a diagram showing Larch arabinogalactan (LAC) end products following 72 hours incubation with 4 subjects' human colonic bacteria. LAG control (solid line) was subjected to protocol without colonic bacteria. The y-axis is mRIU and the x-axis is retention time in minutes.

Figure 3:
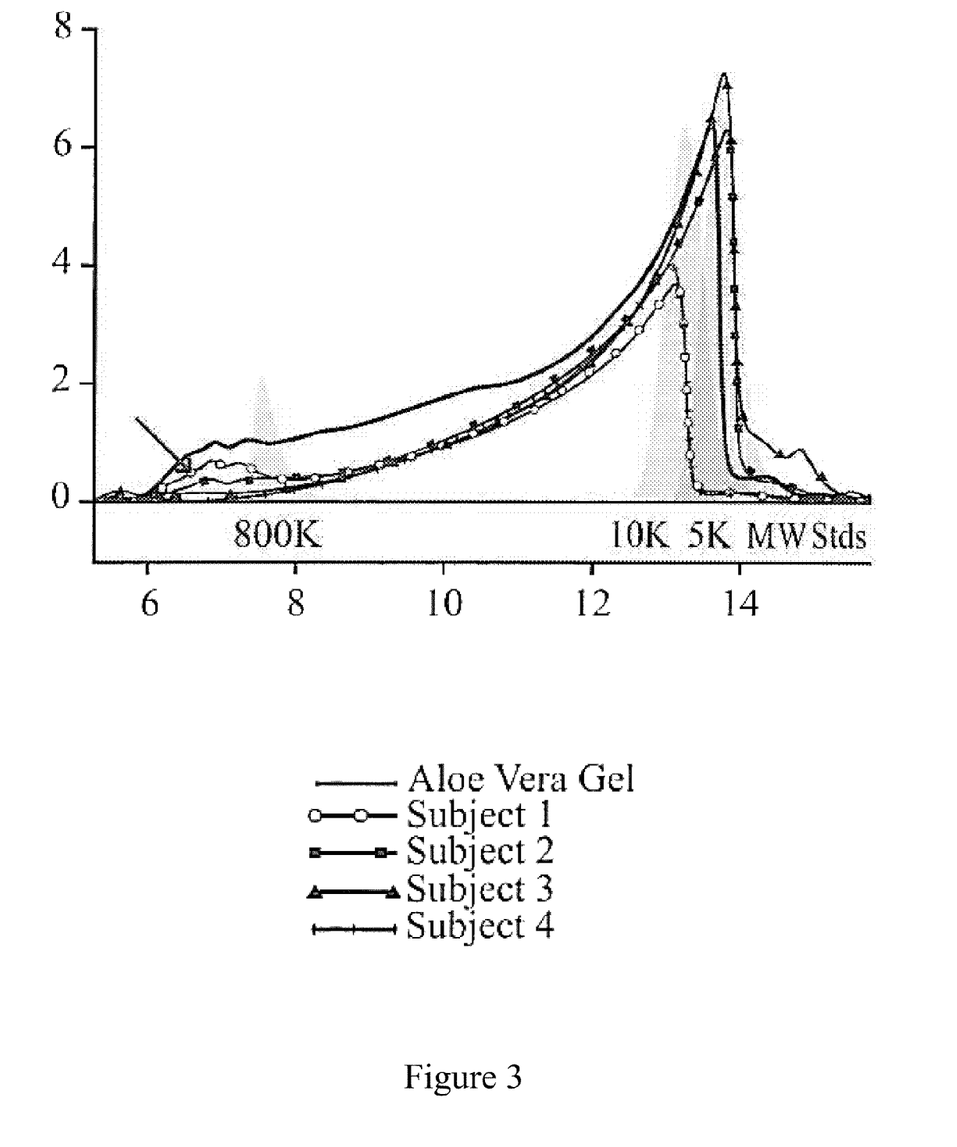
FIG. 3 is a diagram showing Aloe vera gel polysaccharides (AVP) end products following 72 hours incubation with 4 subjects' human colonic bacteria.

Polymeric components of AVP between approximately 1,000,000 and approximately 50,000 MW were almost entirely consumed by fecal bacteria from all subjects, though there was some variability, particularly at the 1,000,000 MW range. Polymers<10,000 were consumed in a highly variable manner by different fecal cultures (FIG. 3). FIG. 3 shows Aloe vera gel polysaccharides (AVP) end products following 72 hours incubation with 4 subjects' human colonic bacteria. AVP control (solid line) was subjected to protocol without colonic bacteria. The y-axis is mRIU and the x-axis is retention time in minutes.

Figure 4:
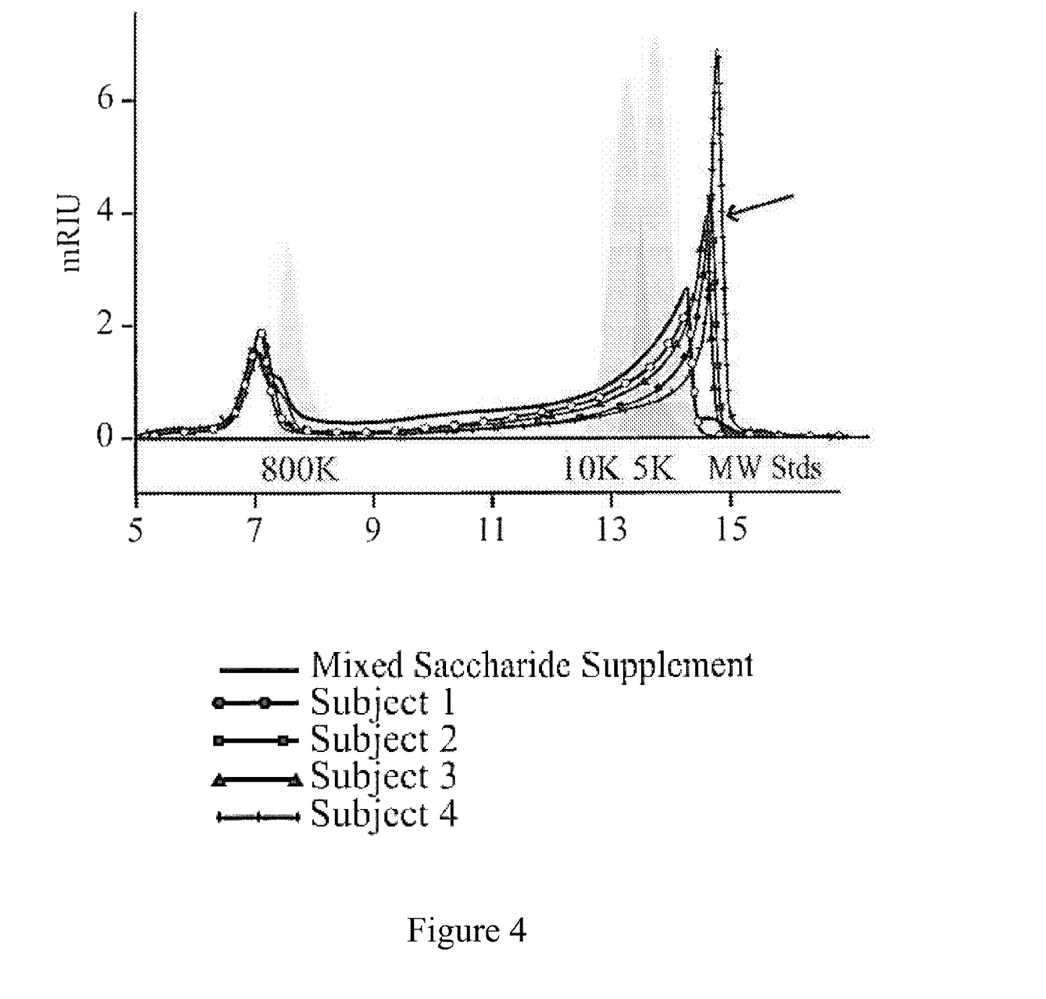
FIG. 4 is a diagram showing mixed saccharide supplement (MSS) end products following 72 hours incubation with 4 subjects' human colonic bacteria.

Polymeric components of MSS of approximately 1,000,000 were not consumed, but polymers between 800,000 to 1,000,000 MW were consumed to varying extents by different cultures selected by MSS. Interestingly, in three subjects, fecal culture degradation of MSS, but not AVP or LAG, resulted in the accumulation or low molecular weight polymers ~1,000 MW that are not found in the control MSS, suggesting the export of glycosidic enzymes that clip small portions of CPPs from parent molecules (FIG. 4). FIG. 4 shows mixed saccharide supplement (MSS) end products following 72 hours incubation with 4 subjects' human colonic bacteria. MSS control (solid line) was subjected to protocol without colonic bacteria.

Discussion. The human intestinal microbiota is thought to include 500~1,000 species, contributing about 1.5 kg biomass. Bacterial utilization of polysaccharides in the in vivo human GI tract is undoubtedly a highly complex process. Polymer degradation is a corporative activity with enzymes from many different bacteria participating in the process. Here, the process of repeated passage of fecal bacteria into fresh media that contained only CPPs as the available carbon source selected for bacteria best able to compare for and utilize CPPs. Bacteria that can use these sugars efficiently will rend to produce more progeny then other species that are less efficient. Over time, these species will dominate the culture. This is the first demonstration to show that *Enteroccus* sp. utilize LAG (Table 1).

LAG was incompletely degraded by all subjects, although there was variability between subjects in their ability to degrade the lower MW (~10,000) portion (FIG. 2, arrow). While oral aloe vera gel has been shown to improve bowel function, this is the first demonstration to illustrate the utilization of aloe vera gel polysaccharides by human colonic bacteria. One finding is that there is greater variation between individuals regarding the ability to utilize high molecular weight (>1,000,000) components of AVP (FIG. 3, arrow). Consumption of very large molecules with limited solubility illustrates that *Enterococcus* sp. can utilize these large molecules. There are several paths that may be used, including internalization of a large CPP panicle with subsequent degradation to smaller constituents. Another is that some bacteria secrete glycosidases, leading to degradation of the large molecules to smaller molecular weight components. Finally, utilization may involve a combination of these processes. *Enterococcus faecalis* is known to encode 21 glycosylhydrolases. This is the first demonstration that utilization of this mixed saccharide dietary supplement (MSS) by human colonic bacteria. A striking illustration is that feeding *E. faecium* MSS leads to the abundant generation of relatively small (~1,000) polymers in the supernatant (FIG. 4, arrow). Since the MSS control is >5,000, generation of lower MW substances must arise from the degradation of larger molecules. This could occur either from degradation of large molecules by enzymes exported to the supernatant by *E. faecium* or from secretion of small polymers by the bacteria themselves. What is quite surprising is that this phenomenon is not observed for either LAG or AVP individually. *Bacteroides* and *Bifidobacteria* sp. were dominant, but *Enterococci* sp.

increased in abundance in the lowest stage of the system. Human colonic degradation of other components of MSS has been investigated. Others have investigated human in vitro fermentation of purified fibers (α and β-linked sulfated fucans) and total algal fibers (α and β-linked alginates) from *U. pinnatifida*. Purified sulfated fucans were not degraded. Forty-seven to sixty-two percent of the alginates were completely metabolized to short chain fury acids. The others concluded that 60% of alginates appear to be degraded by "unusual and unknown" fermentative pathway".

Enrerococclis is ecologically versatile and able to tolerate a wide range of temperatures and pH conditions. It colonizes the human small and large intestines. The two species best able to compete for the three CPPs, *E. faecalis* and *E. faecium*, are popular probiotics. Human probiotic supplementation studies have documented that both species can stimulate the immune system. *E. faecium* supplementation has also been shown to decrease serum cholesterol and reduce the expression of cell receptors involved in the inflammatory response. Greater than 99.9% of the cultivatable bacterial populations in the gut are obligate anaerobes and an estimated 80% of bacteria that reside in the GI tract cannot be cultured under any conditions. The bacterial species present in our day nine cultures represents a relatively small number of species that are able to utilize these CPPs; some species may be able to readily utilize CPPs in vivo but cannot be identified using approaches such as the one used here.

This demonstration is the first to illustrate the utilization by human GI bacteria of the immunomodulatory polysaccharides from aloe vera gel and a mixed saccharide dietary supplement. *Enterococcus* sp. utilized CPPs more efficiently than other species used in this study, leading to their dominance in the culture after repeated passage. MW analysis of CPP end products shows variation in the capability of bacterial biomes recovered from different individuals to use CPP. In vivo subjects were able to completely degrade high MW AVP components; lower MW components were variably consumed. Colonic bacteria feeding on MSS lead to the abundant generation of relatively small (~1,000) polymers, a phenomenon is not observed for either LAG or AVP, two major components of the MSS. Research on these and other CPPs with systems more closely approximating the in vivo GI tract may also be performed by this invention.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Comstock and Coyne (2003) *Bacterioides thetaiotaomicron*: a dynamic, niche-adapted human symbiont. BioEssays 25:926-929

Hooper, et. al. (1999) A molecular sensor that allows a gut commensal to control its nutrient foundation in a competitive ecosystem. Proceedings of the National Academy of Sciences (USA) 96:9833-9838

Stappenbeck, et. al. (2002) Developmental regulation of intestinal angiogenesis by indigenous microbes via Paneth cells. Proceedings of the National Academy of Sciences (USA) 99:15451-15455

Hooper, et. al. (2003) Angiogenins: a new class of microbicidal proteins involved in innate immunity. Nat Immunol 4:269-273

Drisko, et. al. (2003) Probiotics in Health Maintenance and Disease Prevention. Alternative Medicine Review 8(2): 143-155

Salyers, et. al. (1981) Digestion of Larch Arabinogalactan by a strain of Human Colonic Bacterioides Growing in Continuous Culture. J. Agric. Food Chem. 29:475-480.

Mazmanian, et. al. (2005) An Immunomodulatory Molecule of Symbiotic Bacteria Directs Maturation of the Host Immune System. Cell 122:107-118.

Salyers, et. al. (1977) Fermentation of Mucins and Plant Polysaccharides by Anaerobic Bacteria from the Human Colon. Applied and Environmental Microbiology 34:529-533.

Hancock L E, Gilmore M S. Pathogenicity of *Enterococci*. Chapter 25: In: Fischetti V A, Novick R P, Ferretti J J, et al. Gram-Positive Pathogens. ASM Press, 2006.

Xu J, Gordon J I. Honor thy symbionts. Proc Nat Acad Sci USA. 2003; 100 (18):10452-10459.

Madigan M T, Martinko J. Brock Biology of Microorganisms. 11th edition Edition. Pearson/Prentice Hall: Upper Saddle River, 2006.

Foulquie Moreno M R, Sarantinopoulos P, Tsakalidou E, et al. The role and application of enterococci in food and health. Int J Food Microbiol. 2006; 106 (1):1-24.

Ferencik M, Ebringer L, Mikes Z, et al. [Successful modification of human intestinal microflora with oral administration of lactic acid bacteria]. Bratisl.Lek.Listy. 1999; 100 (5):238-245.

Habermann W, Zimmermann K, Skarabis H, et al. [Reduction of acute recurrence in patients with chronic recurrent hypertrophic sinusitis by treatment with a bacterial immunostimulant (*Enterococcus faecalis* Bacteriae of human origin]. Arzneimittelforschung. 2002; 52 (8):622-627.

Hlivak P, Odraska J, Ferencik M, et al. One-year application of probiotic strain *Enterococcus faecium* M-74 decreases serum cholesterol levels. Bratisl.Lek.Listy. 2005; 106 (2): 67-72.

Hlivak P, Jahnova E, Odraska J, et al. Long-term (56-week) oral administration of probiotic *Enterococcus faecium* M-74 decreases the expression of sICAM-1 and monocyte CD54, and increases that of lymphocyte CD49d in humans. Bratisl.Lek.Listy. 2005; 106 (4-5):175-181.

What is claimed is:

1. A method of making a dietary supplement comprising:

mixing isolated polysaccharides with human fecal bacteria comprising *Enterococci* sp. in a bioreactor system under conditions that stimulate the processing of the polysaccharides by the bacteria into processed polysaccharides with reduced molecular weight, wherein the polysaccharides comprise glucomannans and acetylated mannans isolated from Aloe Vera; and preparing the dietary supplement after at least a portion of the isolated polysaccharides have been processed by the bacteria.

2. The method of claim 1, wherein the bacteria process the polysaccharides and the resulting processed polysaccharide are manufactured into a single dosage nutritional supplement.

3. The method of claim 1, further comprising the steps of:

isolating the processed polysaccharides from the natural polysaccharides and the bacteria; and preparing a dosage form comprising the processed polysaccharides.

4. The method of claim 1, further comprising the step of preparing a dosage form comprising the processed polysaccharides, the natural polysaccharides and the bacteria.

5. The method of claim 1, further comprising the processed polysaccharides are loaded into a dosage form selected from powder, capsule, gelcap, tablet, effervescent tablet, liquid or gummy.

6. The method of claim 1, wherein the processed polysaccharides are isolated away from the bacteria, and the processed polysaccharides are loaded into a dosage form selected from powder, capsule, gelcap, tablet, effervescent tablet, liquid or gummy.

7. The method of claim 1, wherein the processed polysaccharides and the bacteria are provided in a sustained release form.

8. The method of claim 1, wherein the polysaccharides are heteropolysaccharides, homopolysaccharides or both.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Chemically Synthesized Oligonucleotide

<400> SEQUENCE: 1
agagtttgat cctggctcag                                              20

<210> SEQ ID NO 2
<211> LENGTH: 19
<212> TYPE: DNA
<213> ORGANISM: Artificial
<220> FEATURE:
<223> OTHER INFORMATION: Chemically Synthesized Oligonucleotide

<400> SEQUENCE: 2
ggttaccttg ttacgactt                                               19
```

9. The method of claim 1, wherein the bacteria are negative for *Clostridium difficile, Salmonella, Shigella, Campylobacter, Vibrio, Yersinia*, and *E. coli O*157.

10. The method of claim 1, wherein the processed polysaccharides are between 1,000 and 10,000 molecular weight.

* * * * *